United States Patent [19]

Zaiger

[11] Plant 5,245

[45] Jun. 12, 1984

[54] NECTARINE TREE—MAY GLO

[76] Inventor: Chris F. Zaiger, 537 Rosemore Ave., Modesto, Calif. 95351

[21] Appl. No.: 449,604

[22] Filed: Dec. 14, 1982

[51] Int. Cl.[3] ..... A01H 5/03

[52] U.S. Cl. ..... Plt./41

[58] Field of Search ..... Plt./41

*Primary Examiner*—Robert E. Bagwill

[57] ABSTRACT

A new and distinct variety of nectarine tree which has a low winter chilling requirement of approximately 300 hours and the tree is of large size, vigorous, spreading growth and a regular and productive bearer of early maturing, large, yellow flesh, clingstone fruit having a high degree of red skin color. The new variety is also characterized by having fruit that colors two to three weeks before ripening and having more highly colored fruit than most early maturing, low chilling varieties.

1 Drawing Figure

ORIGIN OF THE VARIETY

The present variety of nectarine tree was originated by me in my experimental orchard at Modesto, Calif., as a selection from a large number of second generation seedlings which originated from a cross of Fayette peach (non-patented) with the nectarine May Grand, (U.S. Plant Pat. No. 2,794). These seedlings, which were planted and grown under careful observation by me gave many and varing characteristics, one such seedling which is the present variety, having been especially desirable with respect to its fruit and the low chilling requirement of the tree, was selected for asexual reproduction and commercialization.

ASEXUAL REPRODUCTION OF THE VARIETY

The present variety was asexually reproduced by budding in my experimental orchard at Modesto, Calif. and shows that all characteristics come true to the original tree in all respects.

SUMMARY OF THE VARIETY

The present variety of nectarine tree which is of large size, vigorous, spreading growth and being a regular and productive bearer of large, yellow flesh, clingstone fruit with yellow skin, overspread with attractive high red color. The tree is further characterized by having a low winter chilling requirement, approximately 300 hours below 45° Fahrenheit and producing early maturing fruit with good eating quality, and the ability to ship to long distance markets.

PHOTOGRAPHS OF THE VARIETY

The accompanying photographs show typical specimens of the fruit and foliage of my new nectarine variety, with the upper and lower surface of the leaves being illustrated and the exterior and a sectional view of the fruit being shown with a stone remaining in place. The illustrations were taken of the fruit shortly after being picked at maturity (shipping ripe) and the colors are as nearly true as reasonable possible in a color representation of this type.

DESCRIPTION OF THE VARIETY

The following is a botanical description of my new variety of nectarine tree with color terminology (except in common terms) in accordance with Reinhold Color Atlas by A. Kornerup and J. H. Wanscher.

Tree:
- *Size.*—Large.
- *Vigor.*—Vigorous.
- *Form.*—Spreading.
- *Production.*—Productive.
- *Density.*—Dense.
- *Bearing.*—Regular.

Trunk:
- *Size.*—Medium to stocky.
- *Texture.*—Rough to shaggy.

Branches:
- *Size.*—Medium.
- *Texture.*—Smooth to medium rough.
- *Lenticels.*—Medium size. Medium number.
- *Color.*—New growth — reddish brown. Old growth — light brown to brown.

Leaves:
- *Size.*—Large. Average length — 6½" to 8". Average width — 1½" to 2⅛".
- *Texture.*—Smooth.
- *Petiole.*—Medium length.
- *Glands.*—Reniform. Number varies from 2 to 4. Average number 2. Located on base of leaf and upper portion of petiole.
- *Color.*—Upper surface — deep green (27-E-8) to dark green (27-F-7). Lower surface — dull green (27-E4) to (27-E-5).
- *Form.*—Lanceolate. Acutely pointed.
- *Margin.*—Crenate.

Flower buds:
- *Size.*—Large.
- *Length.*—Medium.

Flowers:
- *Blooming period.*—Feb. 11, 1982 to Feb. 28, 1982.
- *Size.*—Large — showy.
- *Pollen.*—Present.
- *Color.*—Pink.

Fruit:
- *Maturity when described.*—Hard ripe.
- *Date of first picking.*—May 28, 1982.
- *Date of last picking.*—June 3, 1982.
- *Size.*—Medium to large. Average diameter axially — 2⅝". Average transversely in suture plane — 2⅝".
- *Form.*—Globose — nearly symmetrical.
- *Suture.*—Shallow.

*Ventral surface.*—Rounded. Only very slightly lipped.

*Cavity.*—Rounded. Average depth — $\frac{3}{8}''$. Average breadth — $\frac{3}{4}''$.

*Apex.*—Rounded. Varied from slight point to slight depression.

Skin:

*Thickness.*—Medium.

*Texture.*—Tough, tenacious to flesh.

*Tendency to crack.*—None.

*Down.*—Wanting.

*Color.*—Yellow ground color (5-A-7) to (5-A-8) overspread with red (9-A-8) to (10-B-8).

Flesh:

*Juice.*—Moderate.

*Texture.*—Firm and meaty.

*Ripens.*—Even.

*Flavor.*—Sub-acid to mild.

*Aroma.*—Very little.

*Eating quality.*—Good.

*Color.*—Yellow (4-A-8) to deep chrome yellow (5-A-8).

Stone:

*Type.*—Clingstone.

*Size.*—Large. Average length — $1\frac{3}{8}''$. Average width — $1\frac{1}{8}''$. Average thickness — $\frac{3}{4}''$.

*Form.*—Ovoid.

*Base.*—Straight to slightly oblique.

*Apex.*—Acute.

*Sides.*—Nearly equal.

*Surface.*—Irregularly furrowed toward apex, pitted toward base.

*Color.*—Light brown (8-D-7) to (8-D-8).

*Tendency to split.*—Very slight.

Use: Dessert.

Shipping quality: Very good.

Keeping quality: Very good.

The tree and its fruit herein described may vary in slight detail due to climatic and soil conditions in which the variety may be grown; the present description being that of the new variety grown under the ecological conditions prevailing at Modesto, Calif.

The following is claimed:

1. A new and distinct variety of nectarine tree with a low winter chilling requirement, approximately 300 hours below 45° Fahrenheit and the tree having vigorous, spreading growth and being a regular and productive bearer of large, yellow flesh, clingstone fruit, maturing 3 to 4 days before Armking Nectarine U.S. Plant Pat. No. 2,943); the fruit is further characterized by its attractive red skin color, good eating quality and the ability to ship to long distance markets.

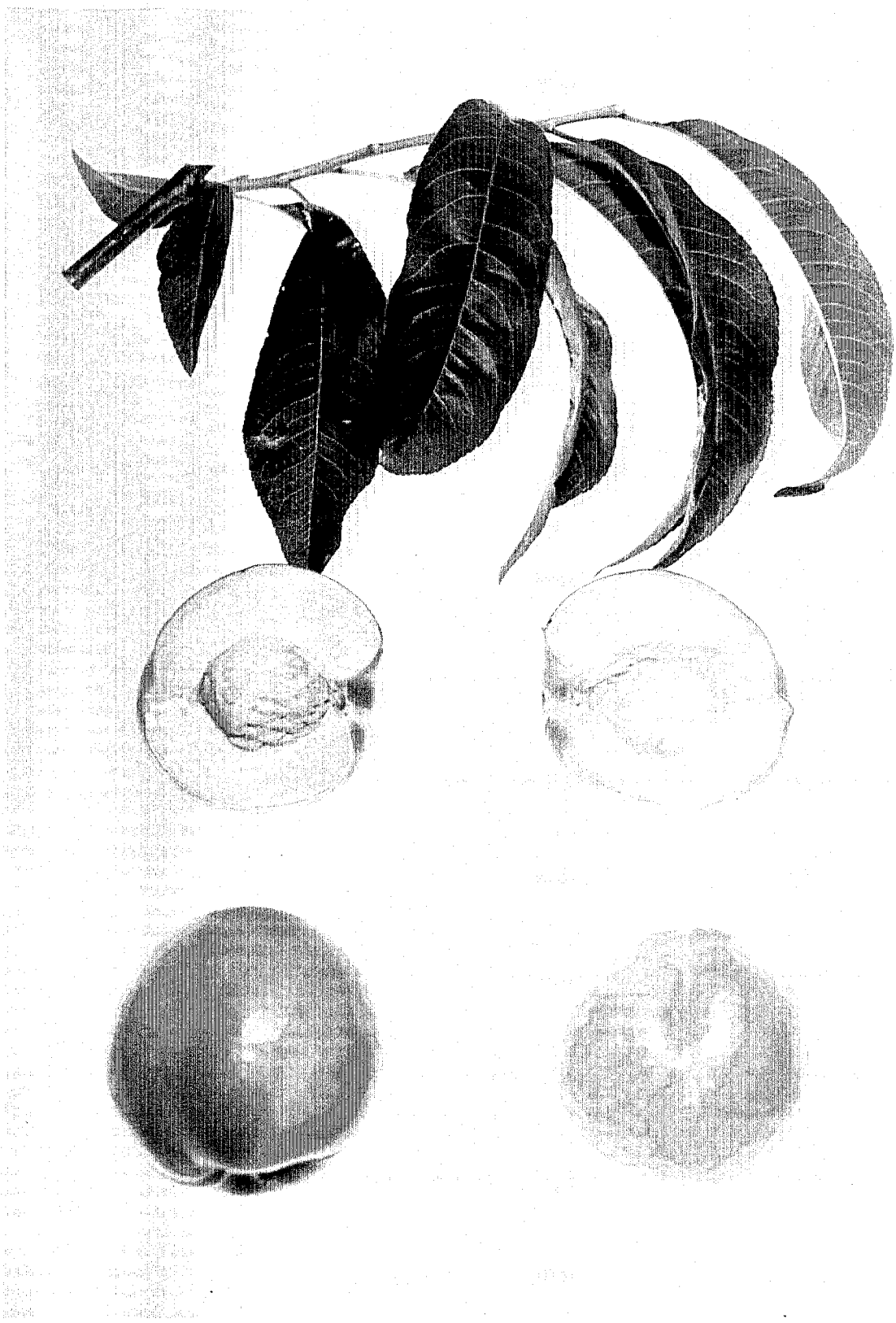

* * * * *